US008628916B2

(12) United States Patent
Kim et al.

(10) Patent No.: US 8,628,916 B2
(45) Date of Patent: Jan. 14, 2014

(54) METHOD FOR ISOLATING HEPATITIS A VIRUS OR SPRING VIREMIA OF CARP VIRUS

(71) Applicant: Industry Foundation of Chonnam National University, Gwangju (KR)

(72) Inventors: Du Woon Kim, Gwangju (KR); Hee Min Lee, Gwangju (KR); Se Young Cho, Yeosu-si (KR); Sang Mu Ko, Busan (KR); Kyung Seo Oh, Gwangju (KR); Joseph Kwon, Jeonju-si (KR); Jong Soon Choi, Daejeon (KR)

(73) Assignee: Industry Foundation of Chonnam National University, Gwangju (KR)

( * ) Notice: Subject to any disclaimer, the term of this patent is extended or adjusted under 35 U.S.C. 154(b) by 0 days.

(21) Appl. No.: 13/703,626

(22) PCT Filed: Oct. 12, 2012

(86) PCT No.: PCT/KR2012/008323

§ 371 (c)(1), (2), (4) Date: Jan. 7, 2013

(87) PCT Pub. No.: WO2013/137527

PCT Pub. Date: Sep. 19, 2013

(65) Prior Publication Data

US 2013/0244221 A1 Sep. 19, 2013

(30) Foreign Application Priority Data

Mar. 15, 2012 (KR) ........................ 10-2012-0026586

(51) Int. Cl.

| | |
|---|---|
| ***C12Q 1/70*** | (2006.01) |
| ***C12Q 1/68*** | (2006.01) |
| ***G01N 33/53*** | (2006.01) |
| ***G01N 33/566*** | (2006.01) |
| ***G01N 33/536*** | (2006.01) |
| ***C07H 21/02*** | (2006.01) |
| ***C07H 21/04*** | (2006.01) |

(52) U.S. Cl.

USPC ............... 435/5; 435/6.12; 435/7.1; 436/501; 436/536; 536/23.1; 536/24.33

(58) Field of Classification Search

None

See application file for complete search history.

(56) References Cited

U.S. PATENT DOCUMENTS 6,942,965 B2 * 9/2005 Pichuantes et al. ............... 435/5
2004/0137430 A1 * 7/2004 Anderson et al. ................. 435/5

OTHER PUBLICATIONS

Monceyron et al. (Journal of Virological Methods. 1994; 46 (2): 157-166, abstract only).*
Reschova et al. (Veterinarni Medicina. 2007; 52 (7): 308-316).*
SEQ ID No. 1 sequence alignment with Genseq accession No. AAV05898. Jul. 1998.*
SEQ ID No. 2 sequence alignment with Geneseq accession No. ADF42260. Feb. 2004.*
SEQ ID No. 3 alignment with Geneseq database accession No. AEB56386 of Chitamber et al. Aug. 2005.*
SEQ ID No. 4 alignment with Geneseq database accession No. ANN35070 of Kaplan et al. Dec. 2007.*
Sang-Mu Ko et al., Detection of Swine Hepatitis A and E Virus in Faeces of Swine Using a Nested RT-PCR, 2011 International Meeting of the Federation of Korean Microbiological Societies, No. 1020, Oct. 13-14, 2011.
M. Koutná et al., Identification of spring viraemia of carp virus (SVCV) by combined RT-PCR and nested PCR, Dis Aquat Org 55: 229-235, 2003.
Eric Dubois et al., Detection and quantification by real-time RT-PCR of hepatitis A virus from inoculated tap waters, salad vegetables, and soft fruits: Characterization of the method performances, International Journal of Food Microbiology 117 (2007) 141-149.
David H. Kingsley et al., Rapid and Efficient Extraction Method for Reverse Transcription-PCR Detection of Hepatitis A and Norwalk-Like Viruses in Shellfish, Applied and Environmental Microbiology, Sep. 2001, p. 4152-4157.

* cited by examiner

*Primary Examiner* — Shanon A Foley
(74) *Attorney, Agent, or Firm* — The PL Law Group, PLLC

(57) ABSTRACT

A method for isolating Hepatitis A virus or Spring viremia of Carp virus. A virus probe is prepared by linking a magnetic bead-conjugated Protein G with an anti-HAV (Hepatitis A Virus) antibody or an anti-rhabdovirus antibody. The virus probe is contacted with a sample to be analyzed to form a virus probe-virus complex. The virus probe-virus complex is then isolated. It may specifically isolate Hepatitis A virus or Spring viremia of Carp virus from a sample mixed viruses.

6 Claims, 4 Drawing Sheets

|  | Mixed virus | Washing out | Eluent |  |
|---|---|---|---|---|
| SVCV PCR | | | | 730bp |
| VHSV PCR | | | | 1.2Kb |

SEQUENCE LISTING

```
<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: HAV_2949F

<400> SEQUENCE: 1

tatttgtctg tcacagaaca atcag                                            25
```

-continued

<210> SEQ ID NO 2
<211> LENGTH: 24
<212> TYPE: DNA
<213> ORGANISM: Artificial Sequence
<220> FEATURE:
<223> OTHER INFORMATION: HAV_3192R

<400> SEQUENCE: 2
aggaggtgga agcacttcat ttga 24

<210> SEQ ID NO 3
<211> LENGTH: 21
<212> TYPE: DNA
<213> ORGANISM: Artificial Sequence
<220> FEATURE:
<223> OTHER INFORMATION: Primer (HAV_dkA24_F)

<400> SEQUENCE: 3
cttcctgagc atacttgagt c 21

<210> SEQ ID NO 4
<211> LENGTH: 19
<212> TYPE: DNA
<213> ORGANISM: Artificial Sequence
<220> FEATURE:
<223> OTHER INFORMATION: Primer (HAV_dkA25_R)

<400> SEQUENCE: 4
ccagagctcc attgaactc 19

<210> SEQ ID NO 5
<211> LENGTH: 25
<212> TYPE: DNA
<213> ORGANISM: Artificial Sequence
<220> FEATURE:
<223> OTHER INFORMATION: Primer (SVCV_F1)

<400> SEQUENCE: 5
tcttggagcc aaatagctca rrtcg 25

<210> SEQ ID NO 6
<211> LENGTH: 24
<212> TYPE: DNA
<213> ORGANISM: Artificial Sequence
<220> FEATURE:
<223> OTHER INFORMATION: Primer (SVCV_R4)
<220> FEATURE:
<221> NAME/KEY: misc_feature
<222> LOCATION: (12)..(12)
<223> OTHER INFORMATION: n is a, c, g, or t

<400> SEQUENCE: 6
ctggggtttc cncctcaaag ytgy 24

<210> SEQ ID NO 7
<211> LENGTH: 23
<212> TYPE: DNA
<213> ORGANISM: Artificial Sequence
<220> FEATURE:
<223> OTHER INFORMATION: Primer (HAV. HEV_EX_F)

<400> SEQUENCE: 7
catggtaaag tgggtcaggg tat 23

<210> SEQ ID NO 8
<211> LENGTH: 20
<212> TYPE: DNA
<213> ORGANISM: Artificial Sequence -continued

```
<220> FEATURE:
<223> OTHER INFORMATION: Primer (HEV_EX_R)

<400> SEQUENCE: 8

agggtgccgg gctcgccgga                                                  20


<210> SEQ ID NO 9
<211> LENGTH: 22
<212> TYPE: DNA
<213> ORGANISM: Artificial Sequence
<220> FEATURE:
<223> OTHER INFORMATION: Primer (HEV_IN_F)

<400> SEQUENCE: 9

gtatttcggc ctggagtaag ac                                               22


<210> SEQ ID NO 10
<211> LENGTH: 23
<212> TYPE: DNA
<213> ORGANISM: Artificial Sequence
<220> FEATURE:
<223> OTHER INFORMATION: Primer (HEV_IN_R)

<400> SEQUENCE: 10

tcaccggagt gyttcttcca gaa                                              23


<210> SEQ ID NO 11
<211> LENGTH: 22
<212> TYPE: DNA
<213> ORGANISM: Artificial Sequence
<220> FEATURE:
<223> OTHER INFORMATION: Primer (SVCV. VHSV_F)

<400> SEQUENCE: 11

caggtcctgg aagcaggaaa aa                                               22


<210> SEQ ID NO 12
<211> LENGTH: 21
<212> TYPE: DNA
<213> ORGANISM: Artificial Sequence
<220> FEATURE:
<223> OTHER INFORMATION: Primer (VHSV_R)

<400> SEQUENCE: 12

cccagaatga ccccgaatag g                                                21


<210> SEQ ID NO 13
<211> LENGTH: 56
<212> TYPE: PRT
<213> ORGANISM: Artificial Sequence
<220> FEATURE:
<223> OTHER INFORMATION: putative VP1/P2A connected proteins antigen
      peptide

<400> SEQUENCE: 13

Glu Ser Met Met Ser Arg Ile Ala Ala Gly Asp Leu Glu Ser Ser Val
1               5                   10                  15

Asp Asp Pro Arg Ser Glu Glu Asp Lys Arg Phe Glu Ser His Ile Glu
            20                  25                  30

Cys Arg Lys Pro Tyr Lys Glu Leu Arg Leu Glu Val Gly Lys Gln Arg
        35                  40                  45

Leu Lys Tyr Ala Gln Glu Glu Leu
    50                  55
```

METHOD FOR ISOLATING HEPATITIS A VIRUS OR SPRING VIREMIA OF CARP VIRUS

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2011/004015, filed on Jun. 1, 2011, which claims priority to Korean Patent Application No. 10-2010-0051892, filed Jun. 1, 2010, entire contents of which are incorporated herein by reference.

BACKGROUND

1. Field of the Invention a. The present invention relates to a method for isolating Hepatitis A virus or Spring viremia of Carp virus.

2. Description of the Related Art

Incidents due to health harm factor of foods derived from agricultural fisheries livestock products seriously affect the health of the people and an economic loss of food poisoning cases caused by absences of appropriate early detection methods and systems is 1.3 trillion won for a year.

Even if virus food poisoning is accounted by 34-40% of the entire food poisoning, loss caused by virus food poisoning is 400 billion won. Therefore, virus diagnostics development research which is available to prevention of virus food poisoning from local agricultural fisheries livestock products and safe food production for consumers and producers, is a method to preventable these social losses in advance.

Although sanitary conditions of modern urban environment have been very improved, it has been reported that antibody retention rate for Hepatitis A virus (HAV) is lowered and that is result to viral hepatitis cases is continuing to decline, whereby virus infection cases is continuing to increase.

Cases of Hepatitis A virus (HAV) detection in specimen from agricultural products including fruits and vegetables have been reported in internal and external. However, the developed diagnosis methods for Hepatitis are A virus (HAV) have been limited in developments of the test methods through mainly enzyme immunoassay using monoclonal or polyclonal antibodies and biological tests so that they are unsuitable for the final user in the field to use and only carried out in parts of groundwater, seafood, meat products and vegetables. In addition, main viral diseases of carp and olive flounder (*Paralichthys olivaceus*) are viral hemorrhagic septicemia (VHS) and spring viremia of carp (SVC). The SVC is a disease occurred in the period increasing temperature from 7° C. to 14° C. It is becoming the global issue because of its strong toxicity and infectiousness. Although SVCV virus which is cause of the SVC has been detected in cultured carp in Korea, there is no extensive damage caused by the SVC so far. Because it is anticipated that the damage due to the SVC should be increased in future, appropriate measures are urgently needed. However, distinct therapeutic measures for viral diseases have been not established yet. In addition, in the case of survive fishes suffered from virus diseases, viruses are remained in their body so that they may be acted as virus carrier which may be consistently troubled. Therefore, it is anticipated that the spread and damage of the virus diseases should be increased. Accordingly, early diagnoses through understanding of the infection status of the virus in aquafarm are urgently needed on obtaining food sources.

Virus purification methods and molecular diagnostics for agricultural fisheries livestock products currently in use have limitations as follows:

First, typical virus purification was a manner that viruses are inoculated into the host cell and cultured with passage to dilute other species such that plenty of the target species are cultured to isolate. However, such the manner was costly and time-consuming.

Second, it is possible to misjudge to non-contamination although viruses are actually present, since the various substances are present in food and parts of them act as interfering substance to reaction of molecular specific-gene amplification.

Throughout this application, several patents and publications are referenced and citations are provided in parentheses. The disclosure of these patents and publications is incorporated into this application in order to more fully describe this invention and the state of the art to which this invention pertains.

SUMMARY

The present inventors have made intensive studies to develop a method for detecting Hepatitis A virus or Spring viremia of Carp virus from a sample mixed viruses in quick and accurate manner. As a result, the present inventors have designed an immuno-probe by linking a magnetic bead with an antibody and found a method for isolating in quick and accurate manner.

Other objects and advantages of the present invention will become apparent from the detailed description to follow taken in conjugation with the appended claims and drawings.

In one aspect of the present invention, there is provided a method for isolating Hepatitis A virus or Spring viremia of Carp virus, including:

(a) preparing a virus probe by linking a magnetic bead-conjugated Protein G with an anti-HAV (Hepatitis A Virus) antibody or an anti-rhabdovirus antibody;

(b) contacting a sample to be analyzed with the virus probe to form a virus probe-virus complex; and (c) isolating the virus probe-virus complex.

The step (b) may be performed at room temperature for 1-30 min.

The step (c) may be performed by contacting a magnet to the resultant of the step (b) to isolate the virus probe-virus complex.

The method may further include genetically analyzing the virus of the virus probe-virus complex isolated in the step (c) by a gene amplification.

The gene amplification may be carried out using a primer pair as set forth in SEQ ID NO:1 and SEQ ID NO:2 or a primer pair as set forth in SEQ ID NO:3 and SEQ ID NO:4 to detect Hepatitis A virus.

The gene amplification may be carried out using the primer pair as set forth in SEQ ID NO:1 and SEQ ID NO:2 or the primer pair as set forth in SEQ ID NO:3 and SEQ ID NO:4 by a nested polymerase chain reaction.

The gene amplification may be carried out using a primer pair as set forth in SEQ ID NO:5 and SEQ ID NO:6 to detect Spring viremia of Carp virus.

DETAILED DESCRIPTION

Figure 1:
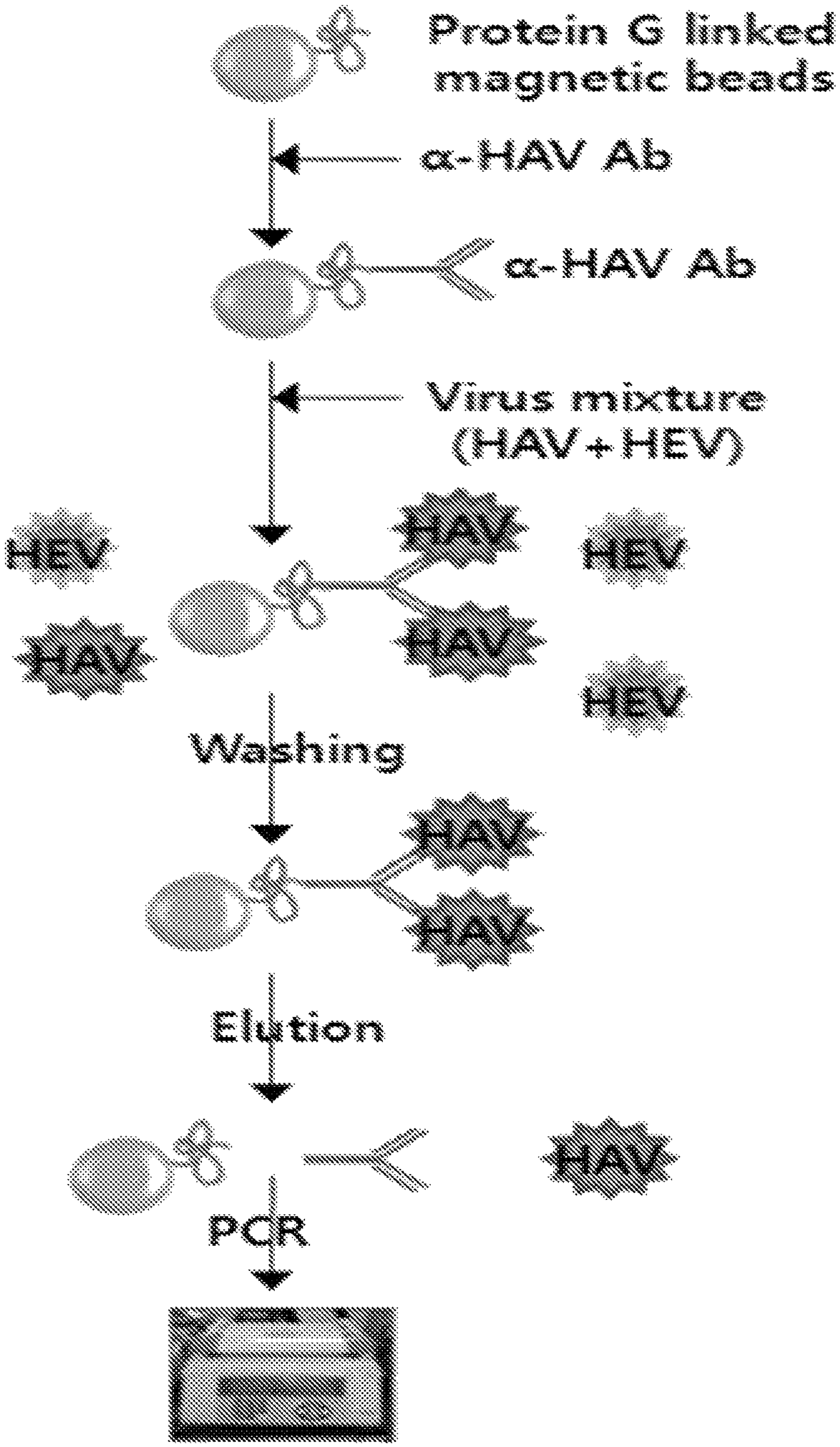
FIG. 1 schematically represents the series of processes of the preparation for the virus probes and the detection for Hepatitis A virus.

The present inventors have made intensive studies to develop a method for detecting Hepatitis A virus or Spring viremia of Carp virus from a sample mixed viruses in quick and accurate manner. As a result, the present inventors have designed an immuno-probe by linking a magnetic bead with an antibody and found a method for isolating in quick and accurate manner.

The method for isolating Hepatitis A virus or Spring viremia of Carp virus in the present invention is explained in detail according to the step as follows:

Step (a): Preparation of a Virus Probe

According to the present invention, a virus probe is prepared by linking a magnetic bead-conjugated Protein G with an anti-HAV (Hepatitis A Virus) antibody or an anti-rhabdovirus antibody.

The anti-HAV (Hepatitis A Virus) antibody or an anti-rhabdovirus antibody are prepared by various methods.

The antibody production may be prepared by a method widely known in the art, such as a fusion method (Kohler and Milstein, European Journal of Immunology, 6:511-519 (1976)), a recombinant DNA methods (U.S. Pat. No. 4,816, 56) or a phage antibody library technique (Clackson et al, Nature, 352:624-628 (1991) and Marks et al, J. Mol. Biol., 222:58, 1-597 (1991)). General process for antibody production is described in Harlow, E. and Lane, D., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; Coligan, CURRENT PROTOCOLS IN IMMUNOLOGY, Wiley/Greene, NY, 1991, and the teachings of which are incorporated herein by reference in its entity. For example, the preparation of the hybridoma cells producing monoclonal antibody is accomplished by fusing immortalized cell line with antibody-producing lymphocytes. This can be done by techniques well known in the art. Polyclonal antibodies may be prepared by injection of the antigen described above to suitable animal, collecting antiserum containing antibodies from the animal, and isolating specific antibodies by any of the known affinity techniques.

In the present invention, the term used herein "antibody" in conjunction with Hepatitis A virus or Spring viremia of Carp virus refers to an antibody which is capable of specifically binding Hepatitis A virus or Spring viremia of Carp virus. The "antibody" binds specifically to the surface protein of Hepatitis A virus or Spring viremia of Carp virus, and includes any antibody fragments as well as the entire antibody.

The entire antibody includes two full-length light chains and two full-length heavy chains, and each light chain is linked to the heavy chain by disulfide bond. The heavy chain constant region includes five different isotypes (y, μ, α, δ and ϵ) of which the subclass is classified into γ1, γ2, γ3, γ4, α1 and α2. The light chain constant region includes two different isotypes (K and λ) (Cellular and Molecular Immunology, Wonsiewicz, M. J., Ed., Chapter 45, pp. 41-50, W. B. Saunders Co. Philadelphia, Pa. (1991); Nisonoff, A., Introduction to Molecular Immunology, 2nd Ed., Chapter 4, pp. 45-65, Sinauer Associates, Inc., Sunderland, Mass. (1984)).

Antigen binding fragment refers to any antibody fragment capable of binding antigen including Fab, F(ab'), $F(ab')_2$ and Fv. Fab has one antigen binding site which is composed of one variable domain from each heavy and light chain of the antibody, one constant region of light chain and the first constant region ($C_{H1}$) of heavy chain. Fab' is different to Fab in the senses that there is a hinge region containing one or more cysteine residues at C-terminal of $C_{H1}$ domain of heavy chain. $F(ab')_2$ antibody is produced by forming a disulfide bond between cysteine residues of hinge region of Fab'. Fv is a minimal antibody fragment including one variable region from each heavy and light chain and recombinant technique to prepare a Fv fragment is disclosed in PCT WO 88/10649, PCT WO 88/106630, PCT WO 88/07085, PCT WO 88/07086 and PCT WO 88/09344. Two-chain Fv is linked by non-covalent bond between one variable region of each heavy and light chain, and single-chain Fv is generally linked by covalent bond via a peptide linker between one variable region of each heavy and light chain or is directly linked to each other at C-terminal, forming a dimer such as two-chain Fv. Such antibody fragments may be obtained using a proteolytic enzymes (e.g., a whole antibody is digested with papain to produce Fab fragments, and pepsin treatment results in the production of $F(ab')_2$ fragments), and may be preferably prepared by genetic recombination techniques.

Step (b): Formation of Virus Probe-Virus Complex

Afterwards, the virus probe of step (a) is contacted with a sample to be analyzed to form a virus probe-virus complex.

The term used herein "sample" includes any sample which may be contained a virus. Examples of the sample include animal cells, tissues, blood, plasma, agricultural fisheries livestock products and foods, but are not limited to.

Preferably, the step (b) is performed at room temperature for 1-30 min.

According to an embodiment, the anti-HAV (Hepatitis A Virus) antibody bound to the magnetic bead-conjugated Protein G of the present invention was bound to the putative VP1/P2A connected proteins of HAV surface and the anti-rhabdovirus antibody bound to the magnetic bead-conjugated Protein G of the present invention was bound to the G protein of Spring viremia of Carp virus surface.

Step (c): Isolation of Virus Probe-Virus Complex

Finally, the virus probe-virus complex is isolated from the resultant of the step (b).

Preferably, the step (c) is performed by contacting a magnet to the resultant of the step (b) to isolate the virus probe-virus complex.

According to an embodiment, the virus probe-virus complex isolated from the step (c) is eluted, neutralized to pH 7.5 and verified the virus isolation.

Preferably, the method further includes the step of genetically analyzing the virus of the virus probe-virus complex isolated in the step (c) by a gene amplification.

Where the present method is carried out the gene amplification, the gene amplification is executed by PCR using primers.

The term used herein "amplification" refers to reactions for amplifying nucleic acid molecules. A multitude of amplification reactions have been suggested in the art, including polymerase chain reaction (hereinafter referred to as PCR) (U.S. Pat. Nos. 4,683,195, 4,683,202, and 4,800,159), reverse transcription-polymerase chain reaction (hereinafter referred to as RT-PCR) (Sambrook, J. et al., *Molecular Cloning. A Laboratory Manual,* 3rd ed. Cold Spring Harbor Press (2001)), the methods of Miller, H. I. (WO 89/06700) and Davey, C. et al.

(EP 329,822), ligase chain reaction (LCR), Gap-LCR (WO 90/01069), repair chain reaction (EP 439,182), transcription-mediated amplification (TMA; WO 88/10315), self sustained sequence replication (WO 90/06995), selective amplification of target polynucleotide sequences (U.S. Pat. No. 6,410,276), consensus sequence primed polymerase chain reaction (CP-PCR; U.S. Pat. No. 4,437,975), arbitrarily primed polymerase chain reaction (AP-PCR; U.S. Pat. Nos. 5,413,909 and 5,861,245), nucleic acid sequence based amplification (NASBA; U.S. Pat. Nos. 5,130,238, 5,409,818, 5,554,517 and 6,063,603), strand displacement amplification and loop-mediated isothermal amplification (LAMP), but not limited to. Other amplification methods that may be used are described in U.S. Pat. Nos. 5,242,794, 5,494,810, 4,988,617 and in U.S. Ser. No. 09/854,317.

PCR is one of the most predominant processes for nucleic acid amplification and a number of its variations and applications have been developed. For example, for improving PCR specificity or sensitivity, touchdown PCR, hot start PCR, nested PCR and booster PCR have been developed with modifying traditional PCR procedures. In addition, real-time PCR, differential display PCR (DD-PCR), rapid amplification of cDNA ends (RACE), multiplex PCR, inverse polymerase chain reaction (IPCR), vectorette PCR and thermal asymmetric interlaced PCR (TAIL-PCR) have been suggested for certain applications. The details of PCR can be found in McPherson, M. J., and Moller, S. G. *PCR*. BIOS Scientific Publishers, Springer-Verlag New York Berlin Heidelberg, N.Y. (2000), the teachings of which are incorporated herein by reference in its entity.

Where the present method is carried out using primers, the gene amplification is executed to analyze the nucleotide sequence of the present biomarkers. Because the present invention is intended to detect the nucleotide sequence of the present biomarkers, the nucleotide sequence of the present biomarkers in samples to be analyzed (e.g., genomic DNA) is searched to determine MS or DM.

According to an embodiment, the amplification reactions are performed by PCR (polymerase chain reaction) disclosed in U.S. Pat. Nos. 4,683,195, 4,683,202, and 4,800,159.

To verify the isolation of Hepatitis A virus according to the present invention, preferably, the gene amplification is carried out using a primer pair as set forth in SEQ ID NO:1 and SEQ ID NO:2 or a primer pair as set forth in SEQ ID NO:3 and SEQ ID NO:4 to detect Hepatitis A virus and more preferably the gene amplification is carried out by a nested polymerase chain reaction.

To verify the isolation of Spring viremia of Carp virus according to the present invention, preferably, the gene amplification is carried out using a primer pair as set forth in SEQ ID NO:5 and SEQ ID NO:6 to detect Spring viremia of Carp virus.

The features and advantages of the present invention will be summarized as follows:

(a) The present invention provides a method for isolating Hepatitis A virus or Spring viremia of Carp virus in quick and accurate manner.

(b) The present invention may specifically isolate Hepatitis A virus or Spring viremia of Carp virus from a sample mixed viruses.

(c) The present invention may detect a small quantity of viruses using virus-specific antigen-antibody reaction.

EXAMPLES OF THE INVENTION

The present invention will now be described in further detail by examples. It would be obvious to those skilled in the art that these examples are intended to be more concretely illustrative and the scope of the present invention as set forth in the appended claims is not limited to or by the examples.

Examples

Examples 1

Immunoprecipitation Method Using Magnetic Beads

Virus probes of the present invention were prepared by linking magnetic bead-conjugated Protein G as magnetic substance with an anti-HAV (Hepatitis A Virus) antibody using virus diagnostic technique. The manufacturing process of virus probes is as follows: 50 μl of magnetic bead-conjugated Protein G (Invitrogen, USA) was added in 1.5 mL tube and the tube was attached on magnet to remove the supernatant. 10 μg of anti-HAV antibody (Goat anti-HAV HM175 polyclonal antibody, catalog #PAB13966, putative VP1/P2A connected proteins antigen peptide, ESMMSRIAAGDLESS-VDDPRSEEDKRFESHIECRKPYKELRLEVGKQRLKY-AQEEL, SEQ ID NO:13; Abnova) was dissolved in 200 μl of PBS (Phosphate Buffered Saline) containing 0.02% Tween 20 and add into the tube mentioned above to react for 10 min. After completion of the reaction, the tube was attached on magnet to remove the supernatant such that only virus probes linked magnetic bead-conjugated Protein G and antibody were remained. To remove impurities except for virus probes, the resultant was washed with PBS twice and removed the supernatant to prepare virus probes for virus detection.

The reaction condition of HAV and HEV (Hepatitis E Virus) mixed with virus proves is as follows: 1 mL of HAV and HEV was added in the tube containing the prepared virus probes, mixed and reacted at room temperature for 10 min. After completion of the immunoreaction, the tube was attached on magnet to isolate an antigen-antibody complex in which the antibody bound to the magnetic bead-conjugated Protein G was bound to the antigen (virus). The magnetic bead portion is bound to magnet. The supernatant containing non-binding viruses was transferred to a new tube (1.5 mL) for a PCR analysis. 200 μl of the antigen-antibody complex binding Protein G was washed with PBS three times to remove impurities, suspended with 100 μl of PBS and moved to new 1.5 mL tube to remove supernatant. The tube containing the antigen-antibody complex binding Protein G was eluted using eluent (50 mM glycine, pH 2.8) to isolate and the resultant was neutralized with 100 mM Tris solution to pH 7.5 and subjected to Nested RT-PCR to verify purification of HVA (FIG. 1).

Virus probes of the present invention were prepared by linking magnetic bead-conjugated Protein G as magnetic substance with an anti-rhabdovirus antibody using virus diagnostic technique. The manufacturing process of virus probes is as follows: 50 μl of magnetic bead-conjugated Protein G (Invitrogen, USA) was added in 1.5 mL tube and the tube was attached on magnet to remove the supernatant. 10 μg of anti-rhabdovirus antibody (Anti-rhabdovirus antibody was prepared using inoculating purified virus to mouse to obtain polyclonal antibody. The anti-rhabdovirus antibody was provided from Professor Myung Ju Oh, Department of Aqualife Medicine, Chonnam National University) was dissolved in 200 μl of PBS (Phosphate Buffered Saline) containing 0.02% Tween 20 and add into the tube mentioned above to react for 10 min. After completion of the reaction, the tube was attached on magnet to remove the supernatant such that only virus probes including magnetic bead-conjugated Protein G and antibody were remained. To remove impurities except for virus probes, the resultant was washed with PBS twice and removed the supernatant to prepare virus probes for virus detection.

Figure 3:
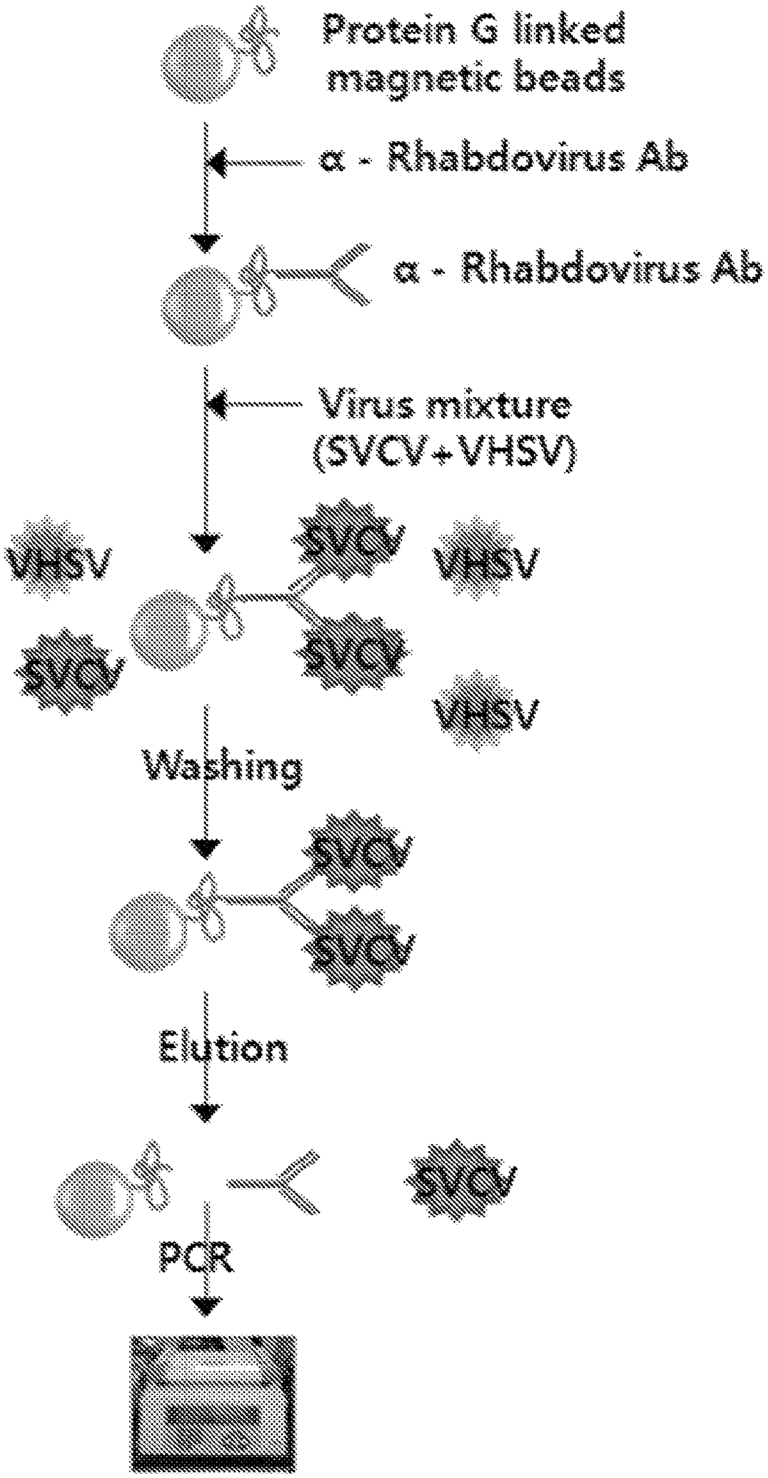
FIG. 3 schematically represents the series of processes of the preparation for the virus probes and the detection for Spring viremia of Carp virus.

The reaction condition of VHSV (Viral Hemorrhagic Septicemia Virus) and SVCV (Spring Viraemia of Carp Virus) mixed with virus proves is as follows: 1 mL of VHSV and SVCV was added in the tube containing the prepared virus probes, mixed and reacted at room temperature for 10 min. After completion of the immunoreaction, the tube was attached on magnet to isolate an antigen-antibody complex in which the antibody bound to the magnetic bead-conjugated Protein G was bound to the antigen (virus). The magnetic bead portion is bound to magnet. The supernatant containing non-binding viruses was transferred to a new tube (1.5 mL) for a PCR analysis. 200 μl of the antigen-antibody complex binding Protein G was washed with PBS three times to remove impurities, suspended with 100 μl of PBS and moved to new 1.5 mL tube to remove supernatant. The tube containing the antigen-antibody complex binding Protein G was eluted using eluent (50 mM glycine, pH 2.8) to isolate and the resultant was neutralized with 100 mM Tris solution to pH 7.5 and subjected to Nested RT-PCR to verify purification of SVCV (FIG. 3).

Examples 2

Verification of Hepatitis A Virus Purification

To verify purification of target virus from virus mixture with immunoprecipitation using magnetic beads, the eluted resultant was subjected to Nested RT-PCR to detect virus. To identify virus, PCR was performed using primer specific for HAV and HEV. The sequences of the primer used in the identification are as follow: HAV_2949F (5'-TAT TTG TCT GTC ACA GAA CAA TCA G-3') (SEQ ID NO: 1) and HAV_3192R (5'-AGG AGG TGG AAG CAC TTC ATT TGA-3') (SEQ ID NO: 2) were used for identification of HAV. HEV_EX_F (5'-CAT GGT AAA GTG GGT CAG GGT AT-3') (SEQ ID NO: 7) and HEV_EX_R (5'-AGG GTG CCG GGC TCG CCG GA-3') (SEQ ID NO: 8) were used for identification of HEV. HAV_dkA24_F (5'-CTT CCT GAG CAT ACT TGA GTC-3') (SEQ ID NO: 3), HAV_dkA25_R (5'-CCA GAG CTC CAT TGA ACT C-3') (SEQ ID NO: 4), HEV_IN_F (5'-GTA TTT CGG CCT GGA GTA AGA C-3') (SEQ ID NO: 9) and HEV_IN_R (5'TCA CCG GAG TGY TTC TTC CAG AA-3') (SEQ ID NO: 10) were used for Nested RT-PCR.

Figure 2:
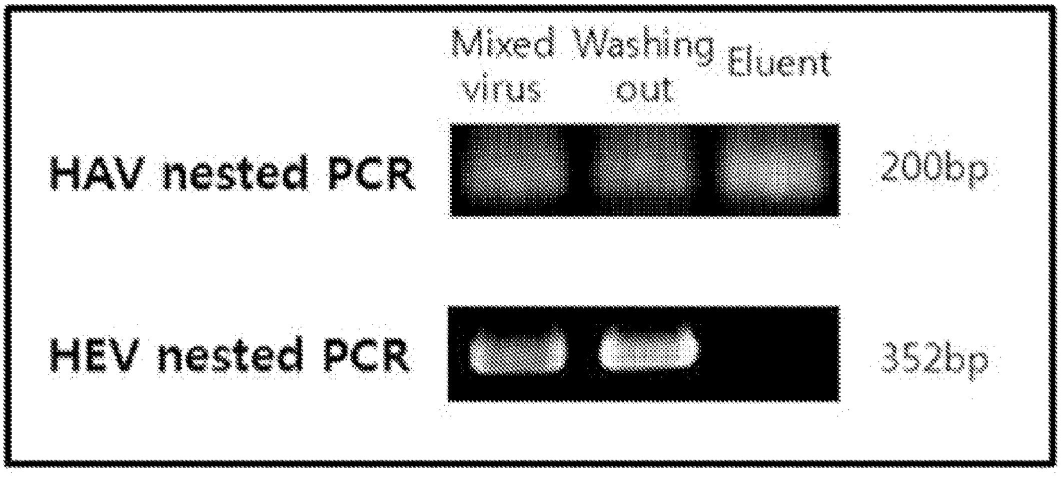
FIG. 2 represents results that Hepatitis A virus isolated from virus probe-virus complex was eluted and verified using Nested PCR.

PCR condition for virus verification is as follows: PCR reaction mixture for HAV was denatured for 30 sec at 94° C., subjected to 40 cycles of 1 min at 60° C., 1 min at 72° C. and extended finally for 10 min at 72° C. Nested RT-PCR reaction mixture for HAV was denatured for 30 sec at 94° C., subjected to 40 cycles of 1 min at 50° C., 1 min at 72° C. and extended finally for 10 min at 72° C. PCR reaction mixture for HEV was denatured for 30 sec at 94° C., subjected to 40 cycles of 1 min at 61° C., 30 sec at 72° C. and extended finally for 10 min at 72° C. Nested RT-PCR reaction mixture for HEV was denatured for 30 sec at 94° C., subjected to 35 cycles of 1 min at 61° C., 30 sec at 72° C. and extended finally for 10 min at 72° C. As a result, it was shown that HEV non-bound to anti-HAV antibody and some HAV were removed and HAV bound to anti-HAV antibody was isolated by eluent solution in an antibody-specific manner (FIG. 2).

Examples 2

Verification of Spring Viremia of Carp Virus (SVCV) Purification

To verify purification of target virus from virus mixture with immunoprecipitation using magnetic beads, the eluted resultant was subjected to Nested RT-PCR to detect virus. To identify virus, PCR was performed using primer specific for SVCV and VHSV. The sequences of the primer used in the identification are as follow: SVCV_F1 (5'-TCT TGG AGC CAA ATA GCT CAR RTC G-3') (SEQ ID NO: 5) and SVCV_R4 (5'-CTG GGG TTT CCN CCT CAA AGY TGY-3') (SEQ ID NO: 6) were used for identification of SVCV. VHSV_F (5'-CAG GTC CTG GAA GCA GGA AAA A-3') (SEQ ID NO: 11) and VHSV_R (5'-CCC AGA ATG ACC CCG AAT AGG-3') (SEQ ID NO: 12) were used for identification of VHSV. HAV_dkA24_F (5'-CTT CCT GAG CAT ACT TGA GTC-3') (SEQ ID NO: 3), HAV_dkA25_R (5'-CCA GAG CTC CAT TGA ACT C-3') (SEQ ID NO: 4), HEV_IN_F (5'-GTA TTT CGG CCT GGA GTA AGA C-3') (SEQ ID NO: 9) and HEV_IN_R (5'TCA CCG GAG TGY TTC TTC CAG AA-3') (SEQ ID NO: 10) were used for Nested RT-PCR.

Figure 4:
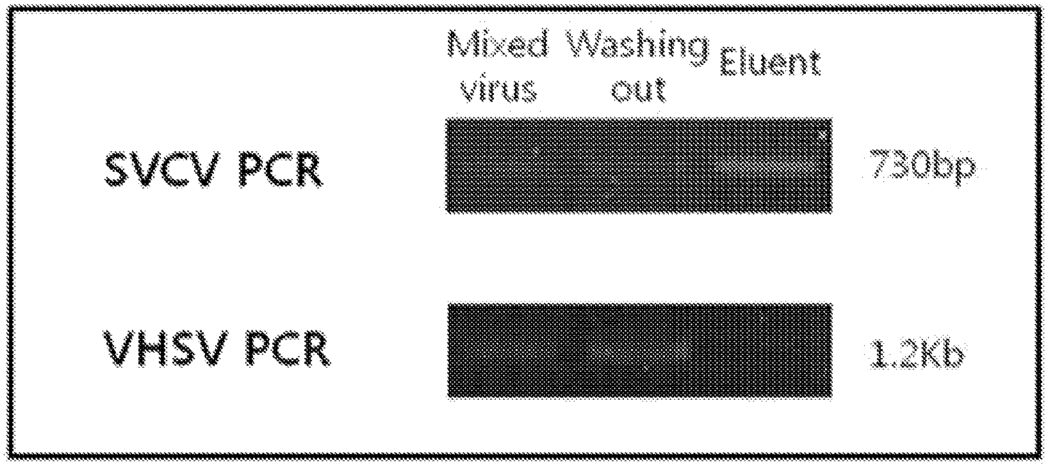
FIG. 4 represents results that Spring viremia of Carp virus isolated from virus probe-virus complex was eluted and verified using RT-PCR.

PCR conditions for SVCV and VHSV detection are as follows: PCR reaction mixture for SVCV was denatured for 1 min at 95° C., subjected to 30 cycles of 1 min at 55° C., 1 min at 72° C. and extended finally for 10 min at 72° C. PCR reaction mixture for VHSV was denatured for 1 min at 95° C., subjected to 30 cycles of 1 min at 58° C., 1 min at 72° C. and extended finally for 5 min at 72° C. As a result, the SVCV band was observed to show that SVCV was isolated (FIG. 4).

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for isolating Hepatitis A virus or Spring viremia of Carp virus, comprising:

(a) preparing a virus probe by linking a magnetic bead-conjugated Protein G with an anti-HAV (Hepatitis A Virus) antibody or an anti-rhabdovirus antibody;

(b) contacting a sample to be analyzed with the virus probe to form a virus probe-virus complex;

(c) isolating the virus probe-virus complex; and (d) analyzing the virus of the virus probe-virus complex isolated in the step (c) by a gene amplification, wherein the gene amplification is carried out using a primer pair as set forth in SEQ ID NO:1 and SEQ ID NO:2 or a primer pair as set forth in SEQ ID NO:3 and SEQ ID NO:4 to detect Hepatitis A virus, or wherein the gene amplification is carried out using a primer pair as set forth in SEQ ID NO:5 and SEQ ID NO:6 to detect Spring viremia of Carp virus.

2. The method according to claim 1, wherein the step (b) is performed at room temperature for 1-30 min.

3. The method according to claim 1, wherein the step (c) is performed by contacting a magnet to the resultant of the step (b) to isolate the virus probe-virus complex.

4. The method according to claim 1, wherein the gene amplification is carried out using the primer pair as set forth in SEQ ID NO:1 and SEQ ID NO:2 or the primer pair as set forth in SEQ ID NO:3 and SEQ ID NO:4 to detect Hepatitis A virus.

5. The method according to claim 1, wherein the gene amplification is carried out using the primer pair as set forth in SEQ ID NO:1 and SEQ ID NO:2 or the primer pair as set forth in SEQ ID NO:3 and SEQ ID NO:4 by a nested polymerase chain reaction to detect Hepatitis A virus.

6. The method according to claim 1, wherein the gene amplification is carried out using the primer pair as set forth in SEQ ID NO:5 and SEQ ID NO:6 to detect Spring viremia of Carp virus.

* * * * *